United States Patent [19]

Amselem et al.

[11] 4,400,384

[45] Aug. 23, 1983

[54] 5-O-CYANOBENZYL-4,5,6,7-TETRAHYDRO-THIENO [3,2-c] PYRIDINE METHANESULFONATE AND OTHER NOVEL SALTS THEREOF

[75] Inventors: Armand Amselem, Toulouse; Fernand Eloy, Eaunes; Jean-Pierre Maffrand, Portet, all of France

[73] Assignee: Sanofi, S.A., Paris, France

[21] Appl. No.: 193,906

[22] Filed: Oct. 6, 1980

[51] Int. Cl.³ .................... C07D 513/04; A61K 31/44
[52] U.S. Cl. ..................................... 424/256; 546/114
[58] Field of Search ........................ 546/114; 424/256

[56] References Cited

U.S. PATENT DOCUMENTS 4,051,141 9/1977 Castaigne .......................... 546/114
4,097,482 6/1978 Amselem .......................... 546/114
4,147,787 4/1979 Maffrand .......................... 546/114

Primary Examiner—John M. Ford
Assistant Examiner—Robert C. Whittenbaugh

[57] ABSTRACT

The invention concerns novel 5-o-cyanobenzyl-4, 5, 6, 7-tetrahydrothieno-[3,2-c] pyridine acid addition salts having inhibitory action against blood platelet aggregation without anti-inflammatory activity, and the compositions and methods of use therefor.

26 Claims, No Drawings

5-O-CYANOBENZYL-4,5,6,7-TETRAHYDRO-THIENO [3,2-c] PYRIDINE METHANESULFONATE AND OTHER NOVEL SALTS THEREOF

The present invention relates to certain novel 5-o-cyanobenzyl-4,5,6,7-tetrahydrothieno [3,2-c] pyridine acid addition salts.

THE PRIOR ART

The synthesis of therapeutically interesting 5-benzyl-4, 5, 6, 7-tetrahydrothieno [3,2-c] pyridines and certain acid addition salts thereof such as the chlorohydrates and maleates, was described by J. P. Maffrand and F. Eloy in *Eur. J. Med. Chem.—Chimica Therapeutica*, September–October 1974–9; No. 5, p. 483–486.

The anti-inflammatory activity and activity in the inhibition of blood-platelet aggregation of certain 5-benzyl-4,5,6,7-tetrahydrothieno [3,2-c] pyridines substituted on the phenyl nucleus was disclosed by M. Podesta, D. Aubert and J. C. Ferrand in *Eur. J. Med. Chem.—Chimica Therapeutica*, September–October 1974–9, No. 5, p. 487–490.

German Patentschrift No. 24 04 308, issued Feb. 9, 1978, describes a large number of 4,5,6,7-tetrahydrothieno [3,2-c] derivatives and acid addition salts thereof which have anti-inflammatory activity and activity for the inhibition of blood-platelet aggregation.

Castaigne U.S. Pat. No. 4,051,141 issued Sept. 27, 1977 discloses many 5-benzyl-4,5,6,7-tetrahydrothieno [3,2-c] pyridines having various substituents on the benzyl group, and the acid addition salts thereof, primarily the hydrochlorides, which also have inhibitor action on blood-platelet aggregation and anti-inflammatory activity. These derivatives also exhibit peripheral and cerebral vasodilator action and anti-arrhythmic action.

Amselem U.S. Pat. No. 4,097,482 issued June 27, 1978 describes a class of ortho-substituted 5-benzyl-4,5,6,7-tetrahydrothieno [3,2-c] pyridines and the hydrochloride, fumarate and maleate acid addition salts thereof which have the same combination of inhibitor action against blood-platelet aggregation and anti-inflammatory activity as the other prior art referred to above. These derivatives also exhibit peripheral and cerebral vasodilator action. Derivative No. 7 of this patent, 5-o-cyanobenzyl-4,5,6,7-tetrahydrothieno [3,2-c] pyridine maleate is the closest previously known derivative to the novel salts of the present invention.

SUMMARY OF THE INVENTION

The present invention relates to certain novel 5-o-cyanobenzyl-4,5,6,7-tetrahydrothieno [3,2-c] pyridine acid addition salts. More specifically, the invention relates to a single especially preferred salt of the named pyridine derivative, the methanesulfonate, and to the hydrochloride, nitrate, hemifumarate and hemitartrate salts which are also of considerable interest.

As noted above, U.S. Pat. No. 4,051,141 issued Sept. 27, 1977 to Castaigne (Castaigne '141) and U.S. Pat. No. 4,097,482 to Amselem (Amselem '482), Jan. 27, 1978, disclose salts of pyridine derivatives, including other salts of the derivative referred to above.

The new salts, like those of the Castaigne '141 and Anselem '482 patents, exhibit excellent inhibitor action on blood-platelet aggregation in warm-blooded animals including humans. The new salts, however, differ from the pyridine derivatives disclosed by the Castaigne and Amselem patents, including 5-o-cyanobenzyl-4,5,6,7-tetrahydrothieno [3,2-c] pyridine maleate, derivative No. 7 of the Amselem patent, in lacking anti-inflammatory activity. Thus the salts of the invention offer a highly advantageous alternative where the inhibition of blood-platelet aggregation is desired, but where anti-inflammatory activity and its attendant physiological effects is contraindicated, or unnecessary. The salts of the invention therefore provide a class of comparatively narrow and specific properties. In view of the association of the various properties in the compounds disclosed by Castaigne and Amselem, it was unexpected to find that the salts of the present class had such a different and varied spectrum of useful properties, further described below.

As noted above, the methanesulfonate salt of the specified pyridine derivative is especially interesting pharmacologically and this is due to the unique combination of pharmaceutical activities it exhibits as well as to its lack of certain other pharmaceutical activities which would be contraindicated or unnecessary in the treatment of certain conditions, diseases or individual patients. It is, of course, widely recognized in the healing arts that it is useful to have a selection of medicaments of varying properties with spectra of varying scope in order to deal effectively with the complexity of conditions which must be met in treating any disease, condition, or combination thereof, or particular animal or human patient.

The preferred methanesulfonate salt, referred hereinafter as the MS salt, not only exhibits excellent inhibitory action against blood-platelet aggregation without anti-inflammatory activity, but differs from the related salts of the prior art in other respects. More specifically, the MS salt is also expecially desirable in that it lacks the peripheral and cerebral vasodilator activity of the salts disclosed in the Castaigne '141 and Amselem '482 patents.

On the other hand, the MS salt exhibits anti-thrombic activity, anti-sludge activity, and anti-spasmodic activity which are not known to be exhibited by the prior art referred to above.

Moreover, the MS salt has also been found to potentiate the central nervous system activities of chloral and "Nembutal" (Na or Ca pentobarbital). On the other hand, the MS salt does not modify the effect of oxotremorine or reserpine, either alone or in the presence of ethyl alcohol in the system.

Still further, the MS salt does not exhibit a number of other activities which might be detrimental or unnecessary in the treatment of certain conditions or patients. More specifically, the MS salt exhibits no analgesic activity, no hemostasis activity, and no central nervous system activity per se.

In view of the foregoing, it is apparent that the salts of the present invention differ markedly and unexpectedly from the prior art, and especially from the salts specifically disclosed in the Castaigne '141 and Amselem '482 patents. Moreover, the new salts provide the basis for new medicaments and methods of treatment not contemplated by or available to the prior art.

PREPARATION OF THE SALTS

The salts of the present invention are prepared according to the general procedures of the prior art referred to above and, in particular according to the procedures of Castaigne U.S. Pat. No. 4,051,141 and Amselem U.S. Pat. No. 4,097,482, the entire disclosure of each of which is incorporated herein by reference.

The salts of the invention which were prepared according to the procedures of the prior patents, were obtained in the form and yield, and had the melting points, shown in the following Table.

TABLE

| Material | Empirical Formula | Molecular Weight | Yield | Appearance | Melting Point |
|---|---|---|---|---|---|
| Methanesulfonate | $C_{15}H_{14}N_2S \cdot CH_3SO_3H$ | 350.46 | 90% | White Crystals | 210° C. Instantaneously |
| Hydrochloride | $C_{15}H_{14}N_2S \cdot HCL$ | 290.82 | 70% | White Crystals | 190° C. |
| Nitrate | $C_{15}H_{14}N_2S \cdot HNO_3$ | 317.38 | 96% | White Crystals | 158° C. Decomposition |
| Hemifumarate | $C_{15}H_{14}N_2S \cdot \frac{1}{2} C_4H_4O_4$ | 312.40 | 61% | White Crystals | 141° C. Ethanol |
| Hemitartrate | $C_{15}H_{14}N_2S \cdot \frac{1}{2} C_4H_6O_6$ | 329.40 | 82.5% | White Crystals | 136° C. Ethanol |

The results of toxicological and pharmacological tests reported below demonstrate the low toxicity, excellent tolerance and useful activities of the new salts of the present invention, particularly the inhibitor activity on blood-platelet aggregation, and absence of the anti-inflammatory activity characteristic of the related compounds and salts of the prior art.

TOXICOLOGICAL INVESTIGATION

The preferred methanesulfonate salt of the present invention was tested for acute and sub-acute toxicity and the results obtained on rats and mice by oral, intravenous and intraperitoneal administration are set forth in the tables below.

| $LD_{50}$ 8 hrs. | ACUTE TOXICITY | | |
|---|---|---|---|
| | Oral | Intravenous | Intraperitoneal |
| Mice | 883 mg/Kg | 134.4 mg/Kg | 898 mg/Kg |
| Rats | 228 mg/Kg | 80.2 mg/Kg | 719 mg/Kg |

SUB-ACUTE TOXICITY

These tests were carried out on four groups of 30 rats, 15 males and 15 females in each group; the rats all being type SPF adults. Administration was by the oral route, carried out 5 days per week for a period of 6 consecutive weeks. The daily dosage of the MS salt was as follows:

| Group A | Control - No dosage |
|---|---|
| Group B | 50 mg/Kg |
| Group C | 150 mg/Kg |
| Group D | 300 mg/Kg |

No significant modification of the behavior of the dosed animals was noted as compared to that of the control animals nor was there any death attributable to the administration of the MS salt. On microscopic examination, the principal organs of animals sacrificed either at the end of the test period or 15 days thereafter, were normal in appearance with exception of some signs of gastric intolerance.

Histological examination of the organs showed good tolerance of the MS salt, in general.

Therefore, the investigations demonstrate low toxicity and good tolerance for the preferred methanesulfonate salts. The other salts have similar low toxicity and tolerance.

Further toxicity investigations were carried out on the MS salt by oral administration in dogs. Two groups of 10 adult dogs were selected; one group being used as the control and the second group having the MS salt administered orally in increasing dosages as follows:

| Days 1 to 7 | 33 mg/Kg/day |
|---|---|
| Days 8 to 14 | 66 mg/Kg/day |
| Days 15 to 24 | 100 mg/Kg/day |

No deaths occurred which were attributable to the MS salt although some of the dogs experienced some vomiting. No significant variations in the hematological, blood biochemical or urinary functions of the dogs were observed following this treatment.

Further tests were conducted by intravenous administration of the MS salt to the dogs. In these tests 15 dogs were divided into three groups of 2 male and 3 female dogs each. One group was used as a control; only the 5 ml of 9% aqueous saline vehicle being injected intravenously. The other two groups of dogs received intravenous injections of the MS salt in the same vehicle; one group a 2.5% solution of the MS salt at a dosage of 7.5 mg/Kg and the other group receiving the same solution at a dosage of 15 mg/Kg.

This treatment was continued for a period of 23 consecutive days without the death of any dog.

In view of the foregoing, it has been demonstrated that the MS salt is of low toxicity and well-tolerated by dogs.

PHARMACOLOGICAL AND METABOLIC PROPERTIES OF THE NEW SALTS

Hemodynamic Pharmacology

Investigations have shown that all five of the novel salts of the present invention exhibit very effective inhibitor action against blood-platelet aggregation and, surprisingly, do so without also exhibiting the anti-inflammatory activity which is characteristic of the related derivatives of the prior art.

Moreover, the preferred MS salt also has the advantage of inhibiting blood-platelet aggregation without causing vasodilator action in the system of the animal under treatment.

The MS salt also exhibits anti-thrombotic activity; anti-sludge activity in vitro on red globules and also in vivo when administered orally or intravenously in the rat; and has no hemostasis activity.

General Pharmacology

Further investigations on the pharmacology of the MS salt have shown that it has no influence on the central nervous system of rats and mice per se, although it does potentialize the central nervous system activity of chloral and "Nembutal" (Ca or Na pentobarbital). On the other hand, it does not modify the effects of oxotremorine or reserpine, either when present alone or together with ethyl alcohol in the system.

The MS salt is also free of analgesic properties.

The MS salt has also been found to exhibit anti-spasmodic activity on the musculotropic isolated intestine. The MS salt is free of diuretic activity, and has no hypolipidic, hypocholesterol, or hypoglycemic activity.

The MS salt has also been observed to have cardiovascular depressive action on the rabbit anesthetized for perfusions at high dosages.

CLINICAL STUDIES

The MS salt has been administered to human patients orally in the form of capsules each containing 175 mg of the active salt. Twelve patients were treated in four groups; one group receiving 2 capsules per day (350 mg); a second group receiving 4 capsules per day (700 mg); a third group receiving 6 capsules per day (1050 mg); and the fourth group receiving 8 capsules per day (1400 mg). This regimen was continued for 3 weeks. Clinical tolerance was excellent; no side effects or incidents being noted.

In a second series of tests, the MS salt was again administered orally in the form of capsules containing 175 mg of the active salt. Eleven patients were treated, each patient receiving 4 capsules per day containing a total of 700 mg of MS salt divided in two portions of 350 mg morning and evening, after meals, for 7 days, and on the 8th day in the morning only. Therefore, the total amount of active ingredient (MS salt) was 5250 mg to each subject. Clinical tolerance was excellent and the medicament exhibited very effective inhibitory activity on blood-platelet aggregation as described below.

INHIBITOR ACTION ON BLOOD-PLATELET AGGREGATION

The inhibitor action on blood-platelet aggregation of the salts of the present invention was determined by two different standard methods known to the art.

The first method, involving the use of ADP (adenosine diphosphate), is that of Ferrand J. C., Gaich C., Dumas, A.—EVALUATION DE L' EFFET ANTI-AGREGANT DE LA TICLOPIDINE PAR UNE TECHNIQUE SUR SANG TOTAL. COMM. SOCIETE DE BIOLOGIE DE TOULOUSE (TOULOUSE Feb. 9, 1978), RESUME IN: REV MED TOULOUSE, 1978, 14, (SUPPL. 5) 680, referred to hereinafter as the ADP method.

The second method is that described in Ferrand J. C., Lale A.—NUMERATION ET AGREGATION PLAQUETTAIRE A L AIDE DE L AUTOCOUNTER. APPLICATION A L ETUDE DE LA TICLOPIDINE. COMM. SYMPOSIUM TECHNICON INDUSTRIE (PARIS, June 15, 1978); Ferrand J. C., Lale A.—EVALUATION EX-VIVO DE L AGREGATION PLAQUETTAIRE PAR UNE TECHNIQUE AUTOMATIQUE SUR SANG TOTAL COMM. SOCIETE FRANCAISE DE BIOLOGIE CLINIQUE (PARIS Sept. 28, 1979); and J. C. Ferrand, A. Lale, D. Aubert and G. Barthelemy—APPRECIATION QUANTITATIVE DE L' ACTIVITE ANTI-AGREGANTE DE LA TICLOPIDINE PAR VOIE AUTOMATIQUE. COMM. REUNION DE L' ASOCIATION FRANCAISE DE PHARMACOLOGISTES DIJON (May 2-3, 1980), and is referred to hereafter as the collagen method.

Groups of 10 female rats of the Wistar type were each dosed with one of the base or one of the salts of the invention and with the corresponding maleate salt of Amselem U.S. Pat. No. 4,097,482, at periods of 48 hours, 24 hours and 2 hours prior to drawing blood for testing by the ADP and collagen techniques referred to above. The active medicaments were administered by means of a gastric tube in the form of a 5% aqueous solution of gum arabic. A dosage level of 100 mg/Kg was used for the base, and for the salts an amount was used sufficient to provide the equivalent amount of the base portion of the salt. The results are as follows.

| MEDICAMENT TESTED | BLOOD PLATELET AGGREGATION ADP | | |
|---|---|---|---|
| | 1 mn 30 s | 3 mn | COLLAGEN |
| Controls | 0.29 | 0.40 | 2.53 |
| Methanesulfonate | 0.73 | 0.88 | 0.59 |
| Hydrochloride | 0.82 | 0.82 | 0.84 |
| Nitrate | 0.84 | 0.83 | 0.91 |
| Hemifumarate | 0.76 | 0.82 | 0.42 |
| Hemitartrate | 0.74 | 0.84 | 0.74 |
| Maleate | 0.70 | 0.81 | 0.80 |

While the maleate salt of the prior art also has substantial activity in the inhibition of blood-platelet aggregation, it is not free of anti-inflammatory or vasodilator activity as is the MS salt and, therefore, could not be used where those additional activities are contraindicated.

The salts of the present invention, may be administered by any route known to the prior art to be suitable for such drugs and specifically as directed in the Castaigne '141 and Amselem '482 patents, for all routes and purposes disclosed therein, although they may be used in somewhat larger doses in view of their very low toxicities and excellent tolerance. More specifically, while the compounds and salts of the prior art are generally administered in dosages from about 0.25 g to about 1 g of active medicament per day (or up to 3 g for vasodilator action), the new salts may be used in amounts of up to about 1.5 g or even more per day for the utilities described.

The new salts, like those of the prior art, may be formulated for oral administration as tablets, coated tablets, capsules, drops or syrups with the usual pharmaceutically acceptable carriers, including excipients or adjuvants. As shown above, a preferred dosage unit is a capsule containing about 175 mg of active salt alone or with any desired pharmaceutically acceptable carrier. The new salts may also be formulated as suppositories for rectal administration or as injectable solutions for parenteral administration.

Non-limiting examples of suitable dosage forms are set forth in the Castaigne '141 and Amselem '482 patents, for the various utilities described therein, and such forms and dosages are appropriate with routine adjustment as known in the art for the present salts for their specific utilities which differ from those of the prior art.

What is claimed is:

1. The methanesulfonate acid addition salt of 5-o-cyanobenzyl-4,5,6,7-tetrahydrothieno [3,2-c] pyridine.

2. An acid addition salt of 5-o-cyanobenzyl-4,5,6,7-tetrahydrothieno [3,2-c] pyridine selected from the group consisting of the hydrochloride, nitrate, hemifumarate and hemitartrate salts.

3. The hydrochloride salt of claim 2.

4. The nitrate salt of claim 2.

5. The hemifumarate salt of claim 2.

6. The hemitartrate salt of claim 2.

7. A therapeutic composition having blood-platelet aggregation activity without anti-inflammatory or vasodilator activity, which comprises the methanesulfonate acid addition salt of 5-o-cyanobenzyl-4,5,6,7-tetrahydrothienopyridine in an amount effective to inhibit blood-platelet aggregation, and a pharmaceutically acceptable carrier.

8. A therapeutic composition having blood-platelet aggregation activity without anti-inflammatory or vasodilator activity, which comprises an acid addition salt of 5-o-cyanobenzyl-4,5,6,7-tetrahydrothieno [3,2-c] pyridine selected from the group consisting of the hydrochloride, nitrate, hemifumarate and hemitartrate salts in an amount effective to inhibit blood-platelet aggregation, and a pharmaceutically acceptable carrier.

9. The therapeutic composition of claim 8 comprising the hydrochloride salt.

10. The therapeutic composition of claim 8 comprising the nitrate salt.

11. The therapeutic composition of claim 8 comprising the hemifumarate salt.

12. The therapeutic composition of claim 8 comprising the hemitartrate salt.

13. A therapeutic dosage unit comprising the composition of claim 7 and containing from about 0.025 g to about 0.5 g of said methanesulfonate salt.

14. A therapeutic dosage unit comprising the composition of claim 8 and containing from about 0.025 g to about 0.5 g of said hydrochloride salt.

15. A therapeutic dosage unit comprising the composition of claim 8 and containing from about 0.025 g to about 0.5 g of said nitrate salt.

16. A therapeutic dosage unit comprising the composition of claim 8 and containing from about 0.025 g to about 0.5 g of said hemifumarate salt.

17. A therapeutic dosage unit comprising the composition of claim 8 and containing from about 0.025 g to about 0.5 g of said hemitartrate salt.

18. A method for the treatment of the warm-blooded animal to inhibit blood-platelet aggregation which comprises administering the composition of claim 7 to said animal in an amount effective to inhibit blood-platelet aggregation and causing said inhibition without causing anti-inflammatory or vasodilator activity in said animal.

19. A method for the treatment of a warm-blooded animal to inhibit blood-platelet aggregation which comprises administering the composition of claim 8 to said animal in an amount effective to inhibit blood-platelet aggregation and causing said inhibition without causing anti-inflammatory or vasodilator activity in said animal.

20. The method of claim 19 wherein the active ingredient is said hydrochloride salt.

21. The method of claim 19 wherein the active ingredient is said nitrate salt.

22. The method of claim 19 wherein the active ingredient is said hemifumarate salt.

23. The method of claim 19 wherein the active ingredient is said hemitartrate salt.

24. The method of claim 18 wherein the composition is administered in a dosage of abut 0.025 g to about 1 g of active ingredient per 24 hours.

25. The method of claim 19 wherein the composition is administered in a dosage of abut 0.025 g to about 1 g of active ingredient per 24 hours.

26. A method for the treatment of a warm-blooded animal to inhibit thrombic, sludge or spasmodic activity, which comprises administering the composition of claim 7 to said animal in an amount effective to inhibit at least one of said activities without inducing analgesic, hemostasis or central nervous system activity in said animal.

* * * * *